United States Patent
Yates et al.

(10) Patent No.: US 11,752,121 B2
(45) Date of Patent: Sep. 12, 2023

(54) SMARTCORE COMPOSITIONS AND METHODS

(71) Applicant: NPI, LLC, Oxford, MS (US)

(72) Inventors: Charles Ryan Yates, Memphis, TN (US); Cameron Volpe Fili, Memphis, TN (US); Ling Lin, Memphis, TN (US); Jonathan Chapman, Memphis, TN (US); Hector L. Lopez, Cream Ridge, NJ (US)

(73) Assignee: NPI, LLC, Oxford, MS (US)

( * ) Notice: Subject to any disclaimer, the term of this patent is extended or adjusted under 35 U.S.C. 154(b) by 0 days.

(21) Appl. No.: 17/886,354

(22) Filed: Aug. 11, 2022

(65) Prior Publication Data

US 2022/0378732 A1  Dec. 1, 2022

Related U.S. Application Data

(63) Continuation of application No. PCT/US2021/017819, filed on Feb. 12, 2021.

(60) Provisional application No. 62/976,969, filed on Feb. 14, 2020.

(51) Int. Cl.
| | | |
|---|---|---|
| *A61K 31/197* | (2006.01) | |
| *A23L 33/105* | (2016.01) | |
| *A61P 3/06* | (2006.01) | |
| *A61P 3/10* | (2006.01) | |
| *A61K 31/10* | (2006.01) | |
| *A61K 31/36* | (2006.01) | |
| *A61K 36/185* | (2006.01) | |

(52) U.S. Cl.
CPC .......... *A61K 31/197* (2013.01); *A23L 33/105* (2016.08); *A61K 31/10* (2013.01); *A61K 31/36* (2013.01); *A61K 36/185* (2013.01); *A61P 3/06* (2018.01); *A61P 3/10* (2018.01)

(58) Field of Classification Search
CPC ....... A61K 31/10; A61K 31/36; A61K 31/197
See application file for complete search history.

(56) References Cited

U.S. PATENT DOCUMENTS

| 6,159,507 A | 12/2000 | Igarashi |
| 2007/0014866 A1 | 1/2007 | Hendrix |
| 2012/0172329 A1 | 7/2012 | Kongtawelert |
| 2012/0178712 A1 | 7/2012 | Kongtawelert |

FOREIGN PATENT DOCUMENTS

| CN | 101254187 A | 9/2008 |
| WO | 2004041295 A1 | 5/2004 |

OTHER PUBLICATIONS

International Search Report and Written Opinion for International Application No. PCT/US2021/017819 dated Jun. 8, 2021; 11 pgs.
Sugasini et al., "Dietary docosahexaenoic acid (DHA) as lysophosphatidylcholine, but not as free acid, enriches brain DHA and improves memory in adult mice," Scientific Reports, 2017; 7:11263; 11pgs.
Sugasini et al., "Enrichment of brain docosahexaenoic acid (DHA) is highly dependent upon the molecular carrier of dietary DHA: lysophosphatidylcholine is more efficient than either phosphatidylcholine or triacylglycerol," Journal of Nutritional Biochemistry, 2019; 74; 10 pgs.
Takada et al., "Sesamin prevents decline in exercise capacity and impairment of skeletal muscle mitochondrial function in mice with high-fat diet-induced diabetes," Exp Physiol.; 2015 100.11:1319-1330.
Zhang et al., "Sesamin Ameliorates High-Fat Diet-Induced Dyslipidemia and Kidney Injury by Reducing Oxidative Stress," Nutrients, 2016; 8, 276; 12 pgs.

*Primary Examiner* — Kevin E Weddington
(74) *Attorney, Agent, or Firm* — Umberg Zipser LLP

(57) ABSTRACT

Nutritionally acceptable non-lipid compositions and methods are presented that modulate lipid metabolism, and especially increase LPC concentrations. Consequently, the compositions and methods presented herein will facilitate DHA transport to neural and retinal tissues as well as LA availability for cardiolipin synthesis.

20 Claims, 5 Drawing Sheets

SMARTCORE COMPOSITIONS AND METHODS

This application is a continuation of International Application with the serial number PCT/US21/17819, which designated the US and which was filed Feb. 12, 2021, and which claims priority to our US Provisional patent application with the Ser. No. 62/976,969, which was filed Feb. 14, 2020, both of which are incorporated by reference herein.

FIELD OF THE INVENTION

The present disclosure relates to composition and methods of metabolic modulation, especially as it relates to modulation of polyunsaturated fatty acid (PUFA) metabolism using nutraceutically and pharmaceutically acceptable non-lipid agents.

BACKGROUND OF THE INVENTION

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

There are numerous nutritional supplements known in the art that are intended to modulate or ameliorate conditions associated with an abnormal lipid profile. For example, high blood levels of LDL cholesterol can be managed with red yeast rice compositions, while LDL oxidation can be attenuated using cruciferous sprout extracts. In still further known methods, serum triglycerides can be reduced using compositions comprising pantethine and/or coenzyme A. While many of such known compositions will act to reduce one or more specific lipid components, nutritional intervention to increase desirable lipid components that are essential for proper energy metabolism, membrane composition, and neural and retinal function is significantly more problematic. For example, the modern Western diet is often imbalanced and results in an imbalanced uptake of omega-6 ($\omega$-6) fatty acids relative to omega-3 ($\omega$-3) fatty acids, resulting in enhanced production of, inter alia, pro-inflammatory prostaglandins, leukotrienes, and thromboxanes. To counteract such imbalance, various fish oil supplements have been developed that are rich in $\omega$-3 fatty acids. Unfortunately, due to their hydrophobic nature, $\omega$-3 fatty acids are not readily absorbed per se but require tightly regulated transport and transmembrane delivery mechanisms. Similarly, and particularly where sustained oxidative stress is present, cellular and circulating phosphatidyl choline (PC) levels are depleted as PC is being incorporated into damaged cell membranes. To help restore proper levels of PC, PC can be regenerated from phosphatidylethanolamine (PE) via methylation of the amino group of PE and from lysophosphatidylcholine (LPC) via lysophosphatidylcholine acyltransferase (LPCAT), which in turn will deplete LPC as is schematically illustrated in FIG. 1.

Unfortunately, LPC is central to numerous physiological pathways, and reduced levels of LPC are a hallmark of various diseases and disorders. For example, reduction in metal/cognitive performance, vision impairment, and lack of immune activation have been associated with low concentrations of LPC. Furthermore, diabetes and dyslipidemia are typically tightly correlated with low levels of LPC. Moreover, docosahexaenoic acid (DHA) is an essential fatty acid that is used in neural and retinal tissues, and transport of DHA into those tissues is in form of LPC-DHA via the Mfsd2a transporter. Unfortunately, dietary supplementation with polyunsaturated fatty acids (PUFAs), LPC, DHA, and LPC-DHA is relatively ineffective as these entities are subject to intestinal enzymes, lipid transport proteins, and transesterification.

Various methods of modifying lipid metabolism have been undertaken and include pharmaceutical intervention and nutraceutical treatments. Unfortunately, most pharmaceutical agents have significant undesirable side effects. On the other hand, nutraceutical treatments are often more benign, however, tend to lack significant effect. For example, CN101254187A described treatment of certain aspects of metabolic syndrome using a combination of sesamin and sesamoline at a specific weight ratio. In another example, sesamin was described as ameliorating high-fat diet-induced dyslipidemia and kidney injury by reducing oxidative stress (*Nutrients* 2016, 8, 276; doi:10.3390/nu8050276), and in a further reexample, sesamin was reported to prevent decline in exercise capacity and impairment of skeletal muscle mitochondrial function in mice with high-fat diet-induced diabetes (*Exp Physiol* 100.11 (2015) pp 1319-1330).

Thus, even though various compositions and methods for lipid modulation are known in the art, all or almost all of them suffer from various disadvantages. Consequently, there is a need to provide improved compositions and methods that provide improved lipid modulation, particularly as it relates to maintenance and/or restoration of physiological concentrations of LPC and LPC-DHA.

SUMMARY OF THE INVENTION

The inventors have now discovered non-lipid nutraceutically/pharmaceutically acceptable compositions and methods for metabolic modulation of PUFA metabolism. In especially preferred aspects, the inventive compositions and methods allow for increased delivery of DHA to the cerebral and/or retinal compartment, for modulation of the $\omega$-6 and $\omega$-3 fatty acid profile and increased availability of phosphatidylcholine (PC), as well as for at least partial reduction of dyslipidemia.

In one aspect of the inventive subject matter, the inventors contemplate a composition that comprises a nutritionally or pharmaceutically acceptable carrier in combination with a lignan and a methyl donor where the composition is formulated for oral administration in one or more dosage units. For example, contemplated dosage units may be formulated as a capsule, tablet, or powder, or as a snack bar or drink.

In some embodiments, the lignan is sesamin, sesamolin, sesaminol, episesamin, or is provided in form of a sesame seed extract or a flax seed extract, while the methyl donor is 5-methyl tetrahydrofolate (5-methyl THF), methylsulfonylmethane (MSM), trimethylglycine (TMG), dimethylglycine (DMG), S-adenosylmethionine (SAM-e), or dimethylaminoethanol (DMEA). For example, the lignan may be sesamin and the methyl donor may be methylsulfonylmethane (MSM).

Where desired, contemplated compositions may also include one or more agents that may further impact lipid metabolism, and particularly preferred additional agents include those that are nutritionally and/or pharmaceutically acceptable, including those that stimulate fatty acid oxidation and/or those that downregulate lipogenesis.

Contemplated dosage units will typically comprise between 100-500 mg of the lignan and between 100-1,000 mg of the methyl donor. Viewed from another perspective, the dosage unit will preferably comprise effective amounts of the lignan and the methyl donor to increase lysophosphatidylcholine (LPC) in circulating blood. Similarly, contemplated dosage units may comprise effective amounts of the lignan and the methyl donor to increase a high-density lipoprotein (HDL) cholesterol fraction in circulating blood. Additionally, or alternatively, contemplated dosage units may comprise effective amounts of the lignan and the methyl donor to increase an omega-3 fatty acid fraction relative to an omega-6 fatty acid fraction in circulating blood.

Therefore, in one exemplary embodiment of the inventive subject matter, the inventors contemplate a nutraceutical composition that comprises a nutritionally or pharmaceutically acceptable carrier in combination with (i) a sesame seed extract, sesamin, sesamolin, sesaminol, and/or episesamin; and (ii) 5-methyl tetrahydrofolate (5-methyl THF), methyl sulfonylmethane (MSM), trimethylglycine (TMG), dimethylglycine (DMG), S-adenosylmethionine (SAM-e), and/or dimethylaminoethanol (DMEA).

While not limiting to the inventive subject matter, the lignan of (i) and the methyl donor of (ii) will typically account by weight for the majority of agents in the composition, such as at least 70 wt %, or at least 80 wt %, or at least 90 wt % of a dosage unit of the nutraceutical composition. In further exemplary embodiments, the dosage unit of the nutraceutical composition will typically be between 200 mg and 1,500 mg. For example, a dosage unit of the nutraceutical composition may include between 100-500 mg of the sesame seed extract, sesamin, sesamolin, sesaminol, and/or episesamin, and may include between 100-1,000 mg of the methylsulfonylmethane (MSM), trimethylglycine (TMG), dimethylglycine (DMG), S-adenosylmethionine (SAM-e), and/or dimethylaminoethanol (DMEA).

In still further contemplated aspects of the inventive subject matter, and due to the lipid modulatory effects of contemplated compositions, the inventors contemplate various beneficial methods and uses of the compounds and compositions presented herein. For example, the inventors contemplate a method of increasing docahexaenoic acid (DHA) uptake into the cerebral and/or retinal compartment in which a nutraceutical composition is administered to a subject in need thereof in an amount that is effective to increase the docahexaenoic acid (DHA) uptake into the cerebral and/or retinal compartment. In another example, the inventors contemplate a method of increasing a high-density lipoprotein (HDL) cholesterol fraction in circulating blood in which a nutraceutical composition is administered to a subject in need thereof in an amount that is effective to increase the high-density lipoprotein (HDL) cholesterol fraction in circulating blood. In a further example, the inventors contemplate a method of increasing an omega-3 fatty acid fraction relative to an omega-6 fatty acid fraction in circulating blood in which a nutraceutical composition is administered to a subject in need thereof in an amount that is effective to increase the omega-3 fatty acid fraction relative to the omega-6 fatty acid fraction in circulating blood. In yet another example, the inventors contemplate a method of increasing peroxisome proliferator-activated receptor alpha (PPARα)-mediated fatty acid oxidation and reducing hepatic lipogenesis in which a nutraceutical composition is administered to a subject in need thereof in an amount that is effective to increase the peroxisome proliferator-activated receptor alpha (PPARα)-mediated fatty acid oxidation and to reduce the hepatic lipogenesis. In a still further example, the inventors contemplate a method of increasing mental performance in a subject in which a nutraceutical composition is administered to a subject in need thereof in an amount that is effective to increase the mental performance. Finally, the inventors also contemplate method of improving vision in a subject in which a nutraceutical composition is administered to a subject in need thereof in an amount that is effective to improve the vision.

Among other suitable subjects, preferred subjects include individuals that are diagnosed with a dyslipidemia, reduced blood level of LPC, pre-diabetes, type-II diabetes, mental decline, and/or impaired vision, as well as subjects of at least 50, or 60, or 70, or 80 years of age.

Various objects, features, aspects, and advantages will become more apparent from the following detailed description of preferred embodiments, along with the accompanying drawing in which like numerals represent like components.

DETAILED DESCRIPTION

Figure 1:
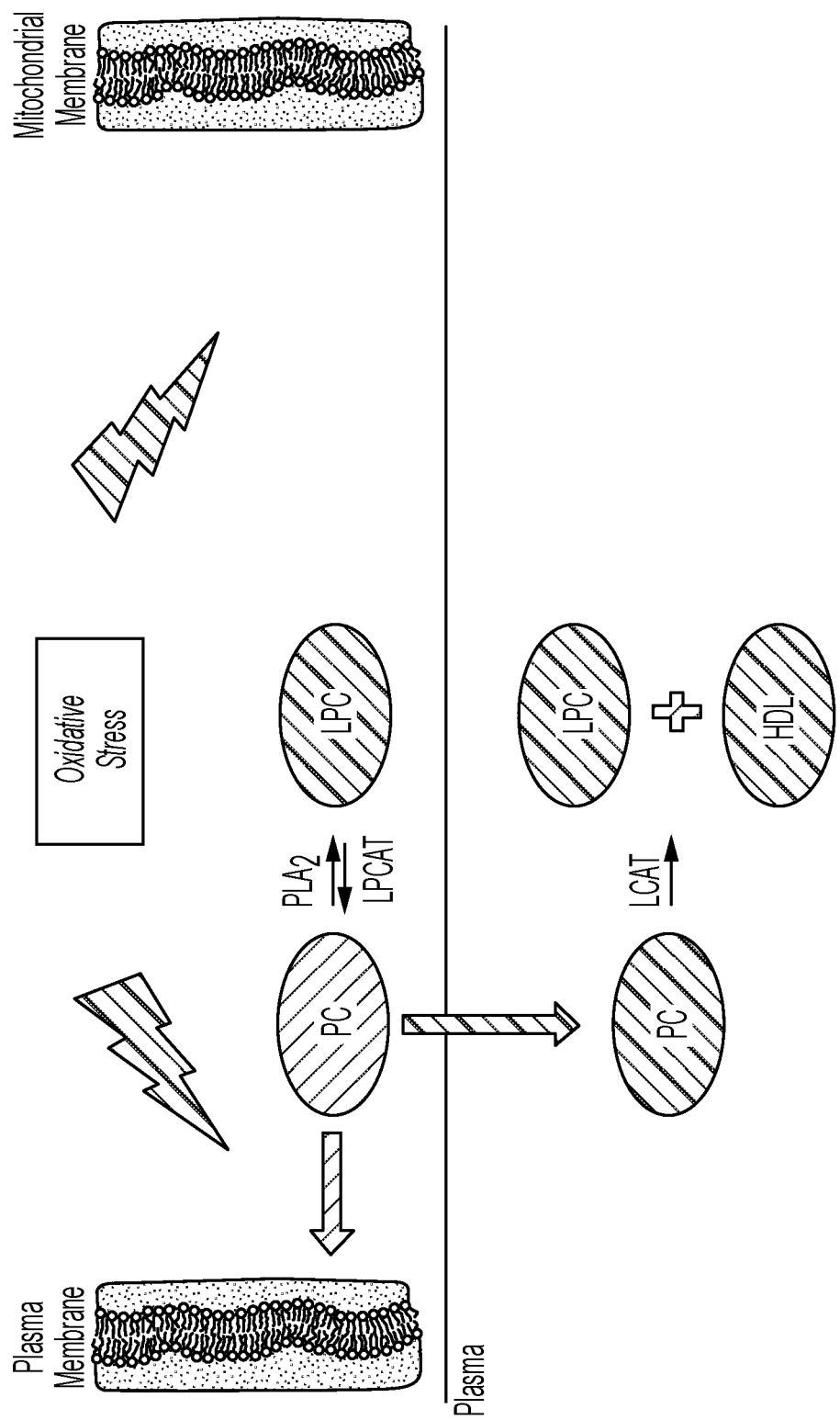
FIG. 1 schematically illustrates effects of oxidative stress on selected lipid pathways.

The inventors have now discovered that a combination of a lignan and a methyl donor can advantageously and significantly modulate lipid metabolism, especially as it relates to LPC, transport of DHA or LA via LPC, and as such increased availability and presence of DHA in neural and retinal tissues and increased synthesis of cardiolipin.

In one exemplary embodiment of the inventive subject matter, a nutraceutical composition is prepared that includes a lignan and a methyl donor in combination with a nutritionally or pharmaceutically acceptable carrier. Most typically, the nutraceutical composition is formulated for oral administration, typically in a single dosage unit such as a tablet, capsule, powder, etc. However, it should be noted that separate administration is also deemed appropriate.

With respect to suitable lignans it is contemplated that all sources of lignans are appropriate and contemplated lignans may therefore be synthetic and purified lignans, and/or partially or fully isolated lignans from a natural source. Thus, especially contemplated lignans include sesame seed extract sesame seed oil, or a flax seed extract or flax seed oil, sesamin, sesamolin, sesaminol, episesamin, and all reasonable combinations thereof. Of course, it should be appreciated that where the lignan is provided as an oil or other extract, the oil or other extract may be in liquid form or complexed in a solid agent (such as a modified or unmodified cyclodextrin), or micro- or nano-encapsulated. Likewise, it should be appreciated that the specific nature of the methyl donor may also vary considerably. However, it is generally preferred that the methyl donor is a naturally occurring methyl donor or a chemical entity that can contribute to physiological availability of methyl groups. Consequently, suitable methyl donors include 5-methyl tetrahydrofolate (5-methyl THF), methylsulfonylmethane (MSM), trimethylglycine (TMG), dimethylglycine (DMG), S-adenosylmethionine (SAM-e), and dimethylaminoethanol (DMEA), and all reasonable combinations thereof. In addition, further contemplated compounds that preserve and/or transfer methyl groups are also deemed suitable for use herein and include Vitamin B12, cobalamins, methylcobalamin, and derivatives thereof, as well as creatine.

For example, where the nutritional composition is formulated as a tablet or capsule, the lignan is sesamin and/or sesame oil while the methyl donor is methylsulfonylmethane (MSM). Most typically, a typical dosage unit of such formulation will comprise between 100-500 mg of the lignan and between 100-1,000 mg of the methyl donor.

However, it should be appreciated that suitable lignan quantities may also be between 0.1-1.0 mg, or between 1.0-10 mg, or between 10-50 mg, or between 50-100 mg, or between 100-200 mg, or between 200-400 mg or between 400-800 mg or between 800-1,200 mg, and even higher in a single dosage unit. On the other hand, where the methyl donor is a cobalamin or 5-methyl tetrahydrofolate (5-methyl THF) or other methyl folate, suitable quantities will be between 1 and 10 mcg, or between 10 and 50 mcg, or between 50 and 100 mcg, or between 100 and 500 mcg, or between 500 and 1,000 mcg, or even higher. Likewise, suitable methyl donor quantities may be between 10-50 mg, or between 50-100 mg, or between 100-200 mg, or between 200-400 mg or between 400-800 mg or between 800-1,200 mg, or between 1,200-2,000 mg, and even higher in a single dosage unit. Viewed from a different perspective, the lignan and the methyl donor will typically be at a weight ratio of between 1:10 and 1:3, or between 1:5 and 1:3, or between 1:3 and 3:1, or between 3:1 and 5:1, or between 5:1 and 10:1. Moreover, it is contemplated that the lignan and the methyl donor contribute together at least 40%, at least 50%, at least 60%, at least 70%, at least 80%, at least 90%, or at least 95% to the total weight of the dosage unit. Regardless of the specific quantities, it is generally preferred that the lignan and the methyl donor are present in relative quantities such that the quantities are synergistic in regard to the in vivo production or serum concentration of LPC, LPC-DHA, and/or LPC-18:2. As will be readily appreciated, synergistic ratios can be readily determined using known analytes such as LPC, LPC-DHA, LPC-18:2 following known protocols in the art.

Figure 2:
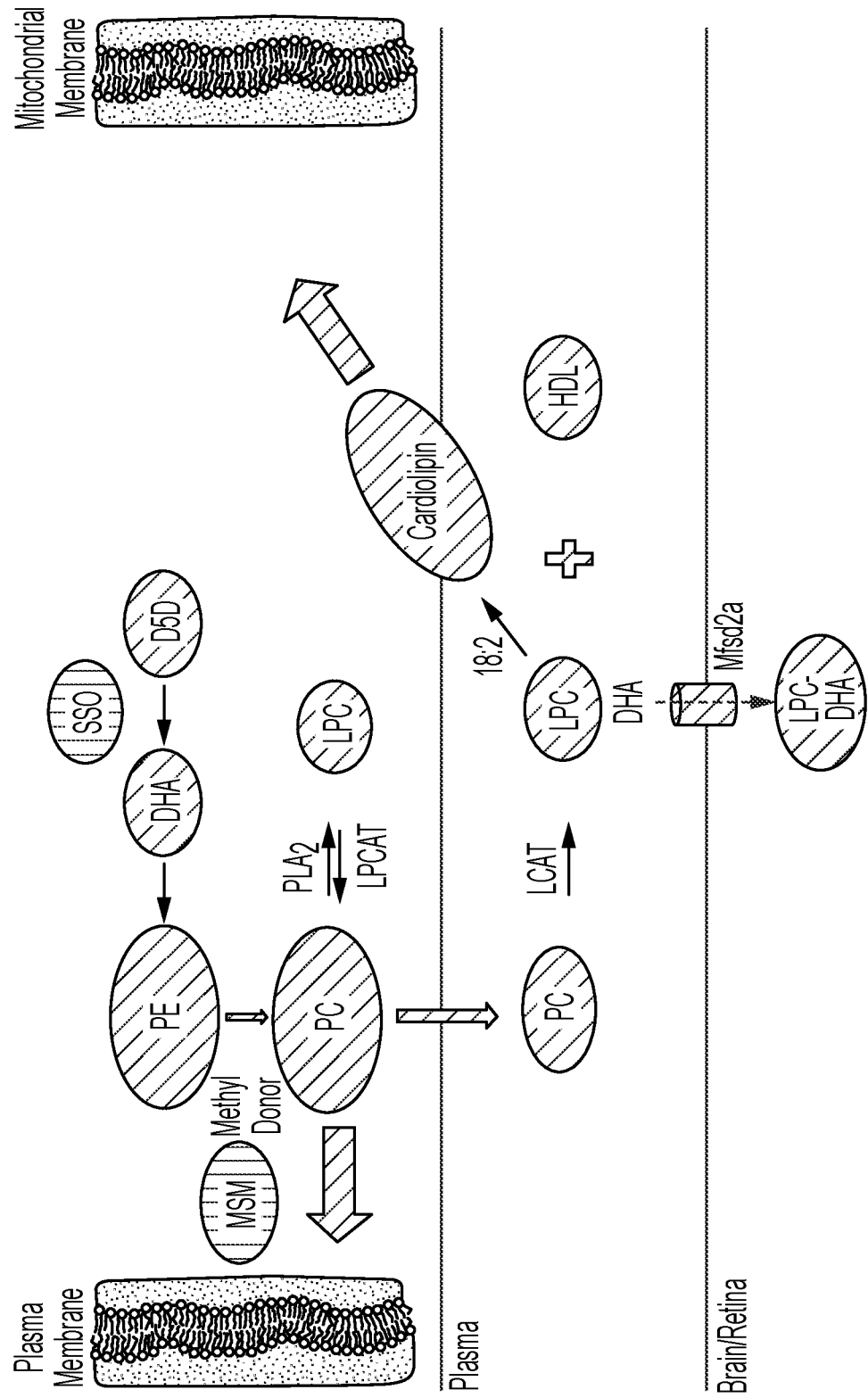
FIG. 2 schematically illustrates effects of sesamin and MSM on selected lipid pathways.

While not limiting to the inventive subject matter, the inventors contemplate that a lignan (e.g., sesamin) and a methyl donor (e.g., MSM) effectively and synergistically influence lipid metabolism via "biased" inhibition of the enzyme delta-5 desaturase (D5D), and so selectively inhibits formation of the pro-inflammatory eicosanoid arachidonic acid (AA) from the dietary omega-6 essential fatty acid (EFA) linoleic acid (LA). This selective inhibition is in turn thought to increase the formation of eicosapentaenoic acid (EPA) and docosahexaenoic acid (DHA) from the omega-3 EFA alpha-linolenic acid (ALA) relative to AA. Increased levels of DHA will so allow for a replenishment of PE that is a major source for PC synthesis. Compounding this beneficial effect, the methyl donor (e.g., MSM) will enhance the conversion of PE to PC and consequently correct a PC deficiency. Thusly increased PC levels are now also available for conversion into LPC, which may now act as a transport form for DHA and 18:2 (required for cardiolipin synthesis in mitochondrial membranes). Sesamin and other lignans are also believed to be preferential or even selective LPCAT inhibitors, which will further enhance intracellular and plasma levels of LPC. FIG. 2 schematically illustrates the synergistic activity of the lignan and the methyl donor.

In addition to the lignan and the methyl donor, additional agents may be included in contemplated formulations that preferably have a regulator role in the lipid metabolism. For example, theacrine, niacinamide, eriocitrin, and/or pantothenate may be included to increase beta oxidation, inhibit de novo lipid synthesis, and/or facilitate PUFA metabolism.

Therefore, and most typically, a dosage unit of the nutraceutical composition according to the inventive subject matter comprises effective amounts of the lignan and the methyl donor to increase lysophosphatidylcholine (LPC) in circulating blood. As LPC will act as a carrier and transport form of DHA, it should be appreciated that the dosage unit will also comprise effective amounts of the lignan and the methyl donor to increase docahexaenoic acid (DHA) uptake into the cerebral and/or retinal compartment (relative to DHA uptake in a subject with reduced LPC levels). Based on further observations (see below), the inventors also contemplate that the dosage unit will comprise effective amounts of the lignan and the methyl donor to thereby increase the high-density lipoprotein (HDL) cholesterol fraction in circulating blood. Viewed from yet another perspective, the dosage unit will comprise effective amounts of the lignan and the methyl donor to increase an omega-3 fatty acid fraction relative to an omega-6 fatty acid fraction in circulating blood.

Most typically, the dosage unit will be administered to the subject (typically human, or farm/companion animal) using the oral route, either in solid form or in liquid form. For example, where the dosage unit is a tablet, capsule, or snack bar, a single or multiple dosage units (e.g., 2, 3, 4, 5, 6, or more) may be taken in a single day. Likewise, where the dosage unit is a powder, a predetermined quantity (e.g., 0.5 g, 1.0 g, 2 g, 5 g, 10 g, etc.) may be administered once or multiple times per diem. Likewise, where the dosage unit is a liquid such as an energy drink, a flavored beverage, a soft drink, soda, or fortified water, the dosage unit will typically be in the range of between 5 mL and 500 mL (e.g., between 5 mL and 10 mL, or between 10 mL and 50 mL, or between 50 mL and 200 mL, or between 200 mL and 500 mL).

In still further preferred aspects, the nutraceutical compositions presented herein may be provided to an individual as a prophylactic agent or agent in support of clinically normal LPC, DHA, and/or HDL cholesterol values. However, it is also contemplated that the compositions presented herein may be used to treat (curative or non-curative) or alleviate or improve signs and symptoms associated with reduced HDL cholesterol, LPC, and/or DHA levels. Therefore, contemplated compositions may be used to increase docahexaenoic acid (DHA) uptake into the cerebral and/or retinal compartment, and with that to improve mental/cognitive performance and/or vision. Further contemplated uses include methods to increase in a high-density lipoprotein (HDL) cholesterol fraction in circulating blood, and/or methods to increase an omega-3 fatty acid fraction relative to an omega-6 fatty acid fraction in circulating blood. In still further contemplated aspects, it should be appreciated that the compositions presented herein may also increase peroxisome proliferator-activated receptor alpha (PPARα)-mediated fatty acid oxidation and/or reduce hepatic lipogenesis.

Viewed from a different perspective, contemplated compositions may therefore be used to increase mental performance in a subject and/or to improve vision in a subject, to increase docahexaenoic acid (DHA) uptake into the cerebral and/or retinal compartment.

EXAMPLES

To validate the inventors' hypotheses on the biological activity of the lignan and methyl donor various animal experiments were performed using mice as test subjects. Diabetes (type 1 and type 2) was used as model disease for LPC deficiency.

Type 1 (T1D) diabetic mice were generated from 8 week old C57BL/6J mice that were treated with streptozotocin 50 mg/kg, 5 days consecutively. Hyperglycemia was confirmed 2 weeks later (BG>250 mg/dl). Upon confirmation, all animals were subjected to 4 week treatment as indicated below. Treatment groups were as follows: Non-diabetic control, Diabetic control, MSM treatment alone, sesamin treatment alone, and MSM+sesamin treatment. For harvest, serum was collected for lipid panel and analyzed using standard clinical protocol and equipment. Tissues (brain, eyes, heart, liver, kidneys) for fatty acid analysis was frozen at −80° C., and liver sections preserved in formalin for histology.

Type 2 (T2D) diabetic mice were 6-week-old BKS.Cg-Dock7m+/+Leprdb/J (db/db), leptin receptor deficient. Hyperglycemia was confirmed (BG>250 mg/dl). Upon confirmation, all animals were subjected to 4-week treatment as indicated below. Treatment groups were as follows: Control, MSM treatment alone, sesame seed oil treatment alone, and MSM+sesame seed oil treatment. For harvest, serum was collected for lipid panel and analyzed using standard clinical protocol and equipment. Tissues (brain, eyes, heart, liver, kidneys) for fatty acid analysis was frozen at −80° C., and liver sections preserved in formalin for histology.

MSM was administered as 1% MSM solution in water: 15-20 ml water was given per ~25 g mouse per day (6-8 g/kg dose for ~25 g mouse; 3-5 g/kg dose for ~40 g mouse). Sesamin was provided as 1.58 mg/mL sesamin in sesame seed oil with 0.12-0.15 mg/g sesamin in mouse food (T1D: 4.4 g food per mouse per day; T2D: 7-8 g food per mouse per day; 20-22 mg/kg dose for mouse (both models)).

Figure 3:
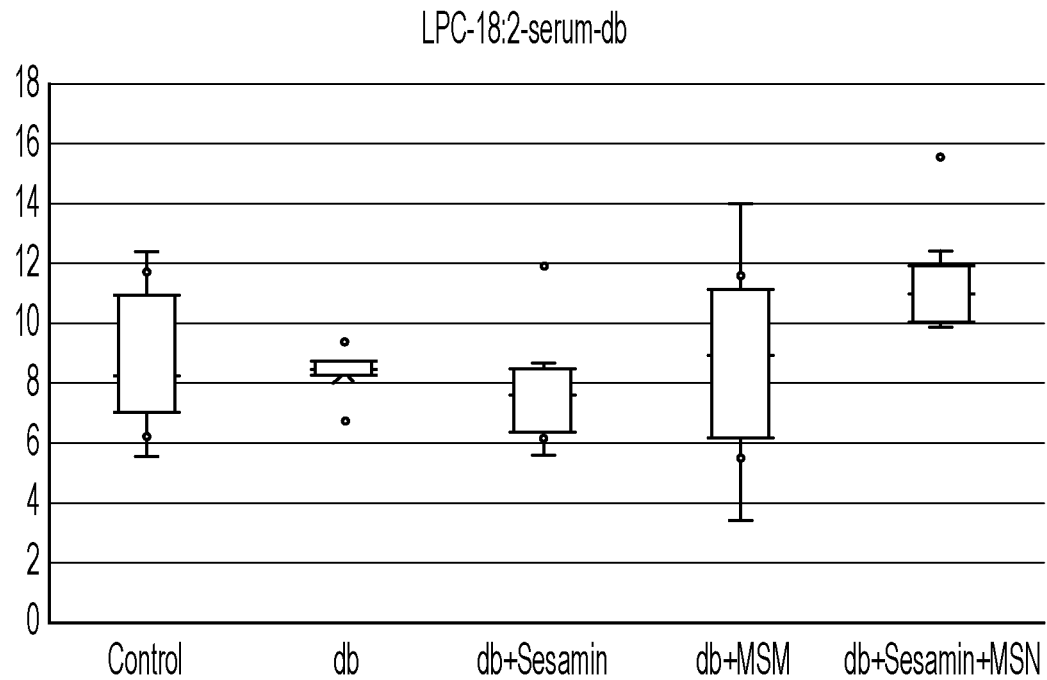
FIG. 3 depicts exemplary results for serum LPC-18:2 post administration of sesamin and MSM.
Figure 4:
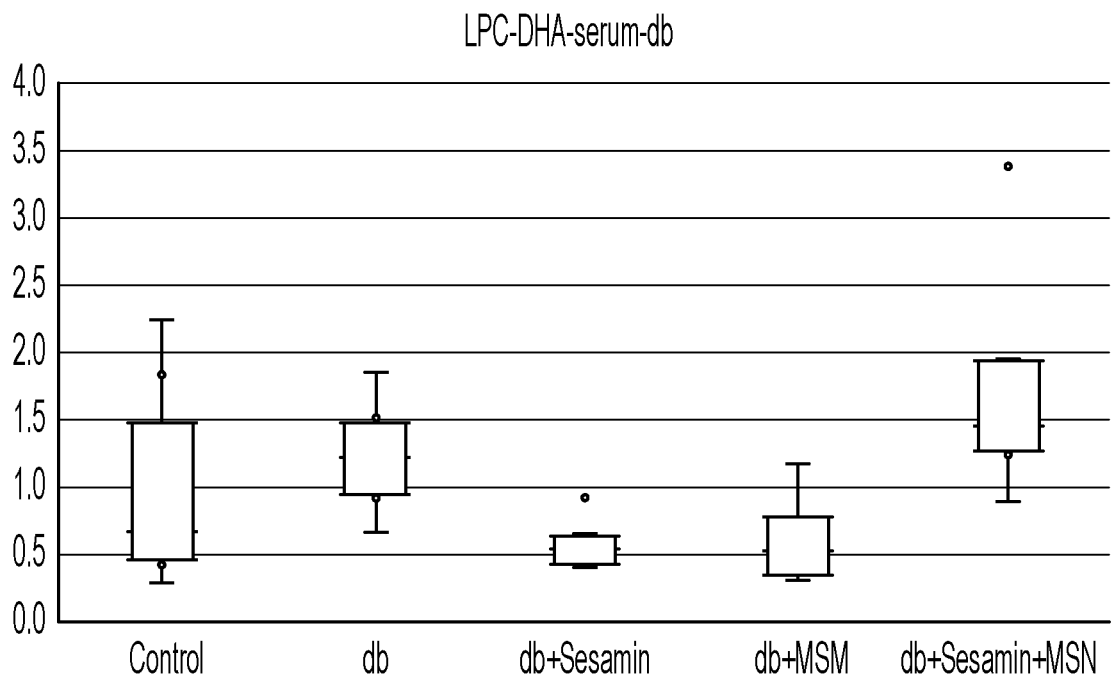
FIG. 4 depicts exemplary results for serum LPC-DHA post administration of sesamin and MSM.

After 4 weeks of administration of the tested compounds in the T2D mouse model, LPC-18:2 and LPC-DHA were determined from plasma and exemplary results are shown in FIG. 3 and FIG. 4, respectively. As can be seen from the results, sesamin and MSM individually did not trigger a statistically relevant change in serum LPC-18:2. However, once co-administered, a clear and synergistic increase in serum LPC-18:2 was observed. Similarly, sesamin and MSM individually did not trigger a statistically relevant change in serum LPC-DHA. However, once co-administered, a clear and synergistic increase in serum LPC-DHA was observed.

Figure 5:
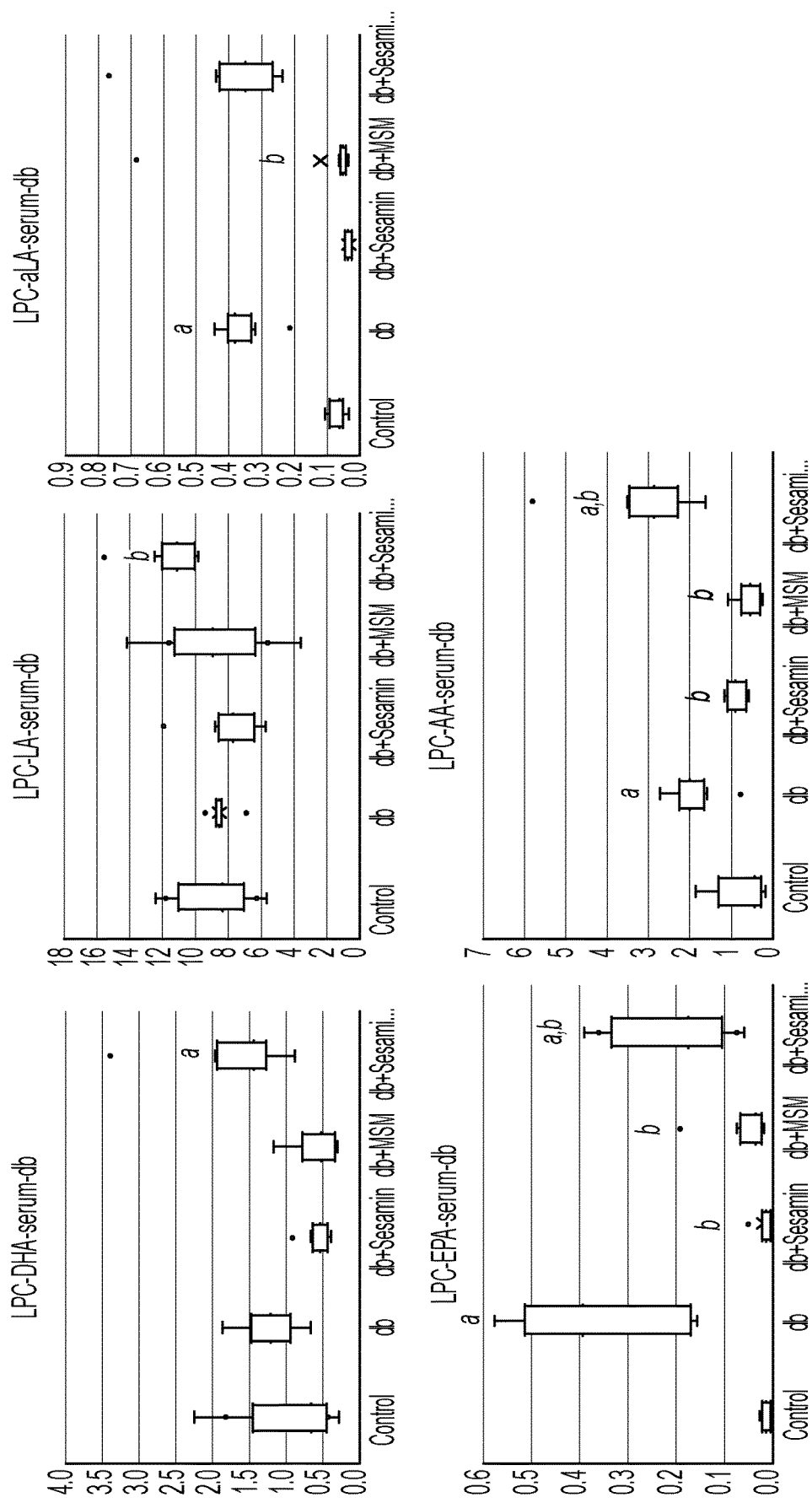
FIG. 5 depicts further exemplary results for selected serum LPC-PUFA post administration of sesamin and MSM.

Further analytic results for selected unsaturated serum LPC-fatty acid levels are shown in FIG. 5. Here, tested analytes were LPC-DHA which once more indicated a strong and synergistic effect for the combination of sesamin and MSM. Likewise, LPC-linoleic acid (18:2) exhibited a strong and synergistic increase in serum concentration only upon co-administration of sesamin and MSM. When α-linolenic acid (aLA) was tested, a substantial synergistic increase in serum concentration was observed only upon co-administration of sesamin and MSM, while sesamin and MSM given individually did not result in an increase. Similar results were seen where the serum LPC-fatty acid was LPC-eicosapentaenoic acid (EPA). Once more, a synergistic increase in serum concentration was observed only upon co-administration of sesamin and MSM, while sesamin and MSM given individually did not result in an increase. Lastly, test results for LPC-arachidonic acid (AA) showed equally notable results in that a synergistic increase in serum concentration was observed only upon co-administration of sesamin and MSM, while sesamin and MSM given individually did not result in an increase.

Figure 6:
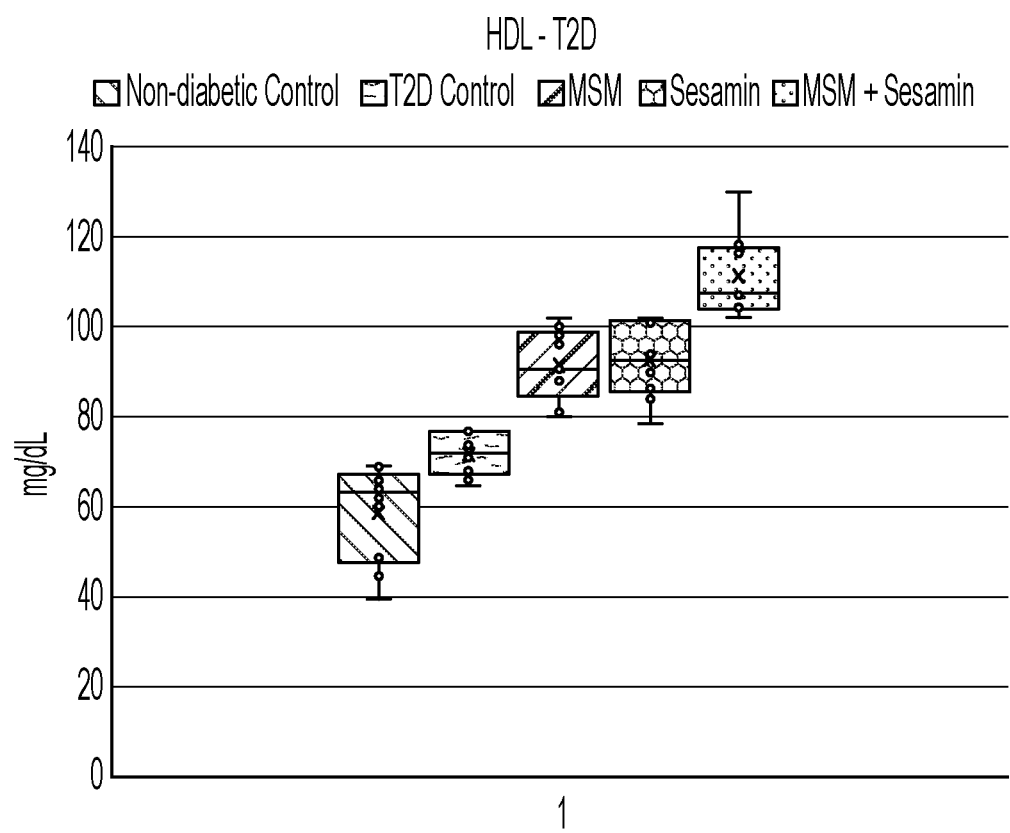
FIG. 6 depicts further exemplary results for HDL-cholesterol post administration of sesamin and MSM.

Further testing for the HDL cholesterol fraction in the T2D model provided further notable synergistic increases where sesamin and MSM were given together as can be seen from the graph in FIG. 6.

Thus, it should be appreciated that various parameters in dyslipidemia (typically associated with a clinically relevant decrease in serum LPC) can be addressed by combined administration of a lignan and a methyl donor. As already noted above, the inventors postulate that such normalization or modulation of LPC, LPC-DHA, and LPC-18:2 is due to the complex interplay between methyl donor availability for PE to PC conversion and inhibitory activity delta-5 desaturase (preferential inhibition towards ω-6 fatty acids) and possibly LPCAT, which in turn increase intracellular and plasma levels of LPC and DHA (free and LPC-DHA).

In still further contemplated uses, the inventors noted that various musculoskeletal and orthopedic, and particularly inflammatory and degenerative conditions of the spine and peripheral joints are associated with dysregulation or imbalances in PUFA metabolism. Consequently, the inventors contemplate that the compositions presented herein may be used for prevention and/or treatment of arthritic conditions.

As used herein, the term "administering" a pharmaceutical or nutraceutical composition or drug refers to both direct and indirect administration of the pharmaceutical/nutraceutical composition or drug, wherein direct administration of the pharmaceutical/nutraceutical composition or drug is typically performed by a health care professional (e.g., physician, nurse, etc.), and wherein indirect administration includes a step of providing or making available the pharmaceutical/nutraceutical composition or drug to the health care professional for direct administration (e.g., via injection, infusion, oral delivery, topical delivery, etc.).

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the full scope of the present disclosure, and does not pose a limitation on the scope of the invention otherwise claimed. No language in the specification should be construed as indicating any non-claimed element essential to the practice of the claimed invention.

It should be apparent to those skilled in the art that many more modifications besides those already described are possible without departing from the full scope of the concepts disclosed herein. The disclosed subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A nutraceutical composition, comprising:
   a nutritionally or pharmaceutically acceptable carrier in combination with a lignan and a methyl donor formulated for oral administration in a single dosage unit;
   wherein the lignan and the methyl donor are present in amounts that, together, upon oral administration to a mammal, synergistically increase serum concentration of LPC, LPC-DHA, LPC-LA, LPC-aLA, LPC-AA, LPC-EPA, and/or HDL cholesterol in circulating blood of the mammal, and
   wherein the lignan is sesamin, sesamolin, sesaminol, episesamin, or is provided in form of a sesame seed extract or a flax seed extract, and wherein the methyl donor is 5-methyl tetrahydrofolate (5-methyl THF), methylsulfonylmethane (MSM), trimethylglycine (TMG), dimethylglycine (DMG), S-adenosylmethionine (SAM-e), or dimethylaminoethanol (DMEA).

2. The nutraceutical composition of claim 1, wherein the lignan is sesamin, sesamolin, or sesaminol, and wherein the methyl donor is methylsulfonylmethane (MSM).

3. The nutraceutical composition of claim 2, wherein the lignan is sesamin or sesame seed oil and wherein the methyl donor is methylsulfonylmethane (MSM).

4. The nutraceutical composition of claim 1, wherein the dosage unit further comprises theacrine, niacinamide, eriocitrin, and/or pantothenate.

5. The nutraceutical composition of claim 1, wherein the dosage unit further comprises pantothenate.

6. The nutraceutical composition of claim 1, wherein the dosage unit further comprises niacinamide.

7. The nutraceutical composition of claim 1, wherein the dosage unit comprises between 100-500 mg of the lignan and wherein the dosage unit comprises between 100-1,000 mg of the methyl donor.

8. The nutraceutical composition of claim 1, wherein the dosage unit comprises respective amounts of the lignan and the methyl donor that increase docahexaenoic acid (DHA) uptake into the cerebral and/or retinal compartment.

9. The nutraceutical composition of claim 1, wherein the dosage unit comprises respective amounts of the lignan and the methyl donor that increase a high-density lipoprotein (HDL) cholesterol fraction in circulating blood by at least 30 mg/dL relative to control.

10. The nutraceutical composition of claim 1, wherein the dosage unit comprises respective amounts of the lignan and the methyl donor that increase an omega-3 fatty acid fraction relative to an omega-6 fatty acid fraction in circulating blood.

11. The nutraceutical composition of claim 1, wherein the dosage unit is formulated as a capsule, a tablet, or a powder.

12. The nutraceutical composition of claim 1, wherein the dosage unit is formulated as a snack bar or a drink.

13. The nutraceutical composition of claim 7, wherein (i) the lignan is a sesame seed extract, sesamin, sesamolin, sesaminol, and/or episesamin; and wherein (ii) the methyl donor is 5-methyl tetrahydrofolate (5-methyl THF), methylsulfonylmethane (MSM), trimethylglycine (TMG), dimethylglycine (DMG), S-adenosylmethionine (SAM-e), and/or dimethylaminoethanol (DMEA).

14. The nutraceutical composition of claim 13, further comprising at least one of theacrine, niacinamide, eriocitrin, and pantothenate.

15. The nutraceutical composition of claim 1, wherein (i) and (ii) account for at least 70 wt % of a dosage unit of the nutraceutical composition.

16. The nutraceutical composition of claim 1, wherein a dosage unit of the nutraceutical composition is between 200 mg and 1,500 mg.

17. The nutraceutical composition of claim 13, wherein a dosage unit of the nutraceutical composition comprises between 100-500 mg of the sesame seed extract, sesamin, sesamolin, sesaminol, and/or episesamin, and wherein the dosage unit comprises between 100-1,000 mg of the methylsulfonylmethane (MSM), trimethylglycine (TMG), dimethylglycine (DMG), S-adenosylmethionine (SAM-e), and/or dimethylaminoethanol (DMEA).

18. The nutraceutical composition of claim 1, wherein the dosage unit comprises between 100-500 mg of the lignan and between 100-1,000 mg of the methyl donor, the lignan is sesamin, and the methyl donor is methylsulfonylmethane (MSM).

19. A nutraceutical composition, comprising:
   a nutritionally or pharmaceutically acceptable carrier in combination with a lignan and a methyl donor formulated for oral administration in a single dosage unit comprising between 100-500 mg of the lignan and between 100-1,000 mg of the methyl donor;
   wherein the lignan and the methyl donor are further present in amounts that, together, upon oral administration to a mammal, synergistically increase serum concentration of at least one of LPC-18:2, LPC-DHA, LPC-aLA, LPC-EPA, and LPC-AA in circulating blood of the mammal, and
   wherein the lignan is sesamin and the methyl donor methyl sulfonylmethane (MSM).

20. The nutraceutical composition of claim 1, wherein:
   the dosage unit comprises between 100-500 mg of the lignan and between 100-1,000 mg of the methyl donor;
   the lignan is sesamin, and:
   the methyl donor is 5-methyl tetrahydrofolate (5-methyl THF), trimethylglycine (TMG), dimethylglycine (DMG), S-adenosylmethionine (SAM-e), or dimethylaminoethanol (DMEA).

* * * * *